United States Patent
Wood et al.

[11] Patent Number: 6,086,615
[45] Date of Patent: *Jul. 11, 2000

[54] PROSTHETIC PYLON HAVING A COMPRESSIBLE MEDIUM TO SUPPORT A PATIENT'S WEIGHT

[75] Inventors: Christopher Wood, Kingston; James G. Cairns, Jr., Bainbridge Island; Walter D. Harris, Bremerton, all of Wash.

[73] Assignee: Seattle Orthopedic Group, Inc., Poulsbo, Wash.

[*] Notice: This patent is subject to a terminal disclaimer.

[21] Appl. No.: 08/939,134

[22] Filed: Sep. 29, 1997

Related U.S. Application Data

[63] Continuation of application No. 08/527,514, Sep. 12, 1995, Pat. No. 5,702,488.

[51] Int. Cl.⁷ .................................. A61F 2/60; A61F 2/62
[52] U.S. Cl. .................. 623/27; 623/35; 248/609
[58] Field of Search ................. 623/27, 32–38, 623/49, 50, 52; 248/125.2, 157, 161, 282.1, 608, 609

[56] References Cited

U.S. PATENT DOCUMENTS

| | | | |
|---|---|---|---|
| 1,783,801 | 12/1930 | Leipert | 267/30 |
| 4,038,705 | 8/1977 | Owens et al. | 623/38 X |
| 5,458,656 | 10/1995 | Phillips | 623/27 |
| 5,702,488 | 12/1997 | Wood et al. | 623/27 |

FOREIGN PATENT DOCUMENTS

| | | | |
|---|---|---|---|
| 1350065 | 12/1963 | France | 623/27 |
| 1 386 333 | 3/1975 | United Kingdom | 623/27 |

*Primary Examiner*—David H. Willse
*Attorney, Agent, or Firm*—Seed and Berry, LLP

[57] ABSTRACT

A pylon includes a first end portion connected to a patient's leg stump and a second end portion connected to a prosthetic foot. The second end portion includes a piston, and the first end portion includes a piston chamber receiving the piston. The second end portion is thus rotatable and axially movable relative to the first end portion about and along a longitudinal axis of the pylon, respectively. The piston chamber encloses a compressible volume of fluid through which substantially all of the patient's weight applied through the patient's leg stump is supported. The compressible volume of fluid is sealed so that it can be pressurized. Also, a torsional spring couples the piston and piston chamber and resists relative rotation between the piston and piston chamber without supporting any substantial portion of the patient's weight applied through the patient's leg stump to the piston. The present invention thus advantageously provides a pylon which is more cushioned and resilient than conventional pylons.

29 Claims, 5 Drawing Sheets

PROSTHETIC PYLON HAVING A COMPRESSIBLE MEDIUM TO SUPPORT A PATIENT'S WEIGHT

CROSS-REFERENCE TO RELATED APPLICATION

This application is a continuation of U.S. patent application Ser. No. 08/527,514, filed Sep. 12, 1995, now U.S. Pat. No. 5,702,488.

TECHNICAL FIELD

The present invention relates in general to a prosthetic pylon, and in particular to a prosthetic pylon supporting the weight of a patient on an enclosed compressible volume of fluid.

BACKGROUND OF THE INVENTION

Individuals who lose all or part of a leg have a residual leg, stump to which a prosthetic foot is often attached through an elongated pylon. Such a pylon is typically a rigid member made with a material, like a carbon-fiber composite or aluminum, which provides the rigidity necessary to support an individual's weight.

This rigidity can be problematic, because it often makes conventional pylons too stiff for comfortable movement. Each step on such a pylon can be awkward and painful, rather than cushioned and resilient like a natural leg. Therefore, there is a need in the art for a pylon which adequately supports an individual's weight and is more cushioned and resilient than conventional pylons.

SUMMARY OF THE INVENTION

An inventive pylon includes a first end portion connected to a patient's leg stump and a second end portion connected to a prosthetic foot. The second end portion is rotatable and axially movable relative to the first end portion about and along a longitudinal axis of the pylon, respectively. Preferably, the second end portion includes a piston, and the first end portion includes a piston chamber receiving the piston. The piston chamber encloses a compressible volume of fluid through which substantially all of the patient's weight applied through the patient's leg stump is supported. The compressible volume of fluid is preferably sealed so that it can be pressurized. Also, a torsional spring couples the piston and piston chamber and resists relative rotation between the piston and piston chamber without supporting any substantial portion of the patient's weight applied through the patient's leg stump. The present invention thus advantageously provides a pylon which is more cushioned and resilient than conventional pylons.

DETAILED DESCRIPTION OF THE INVENTION

Figure 1:
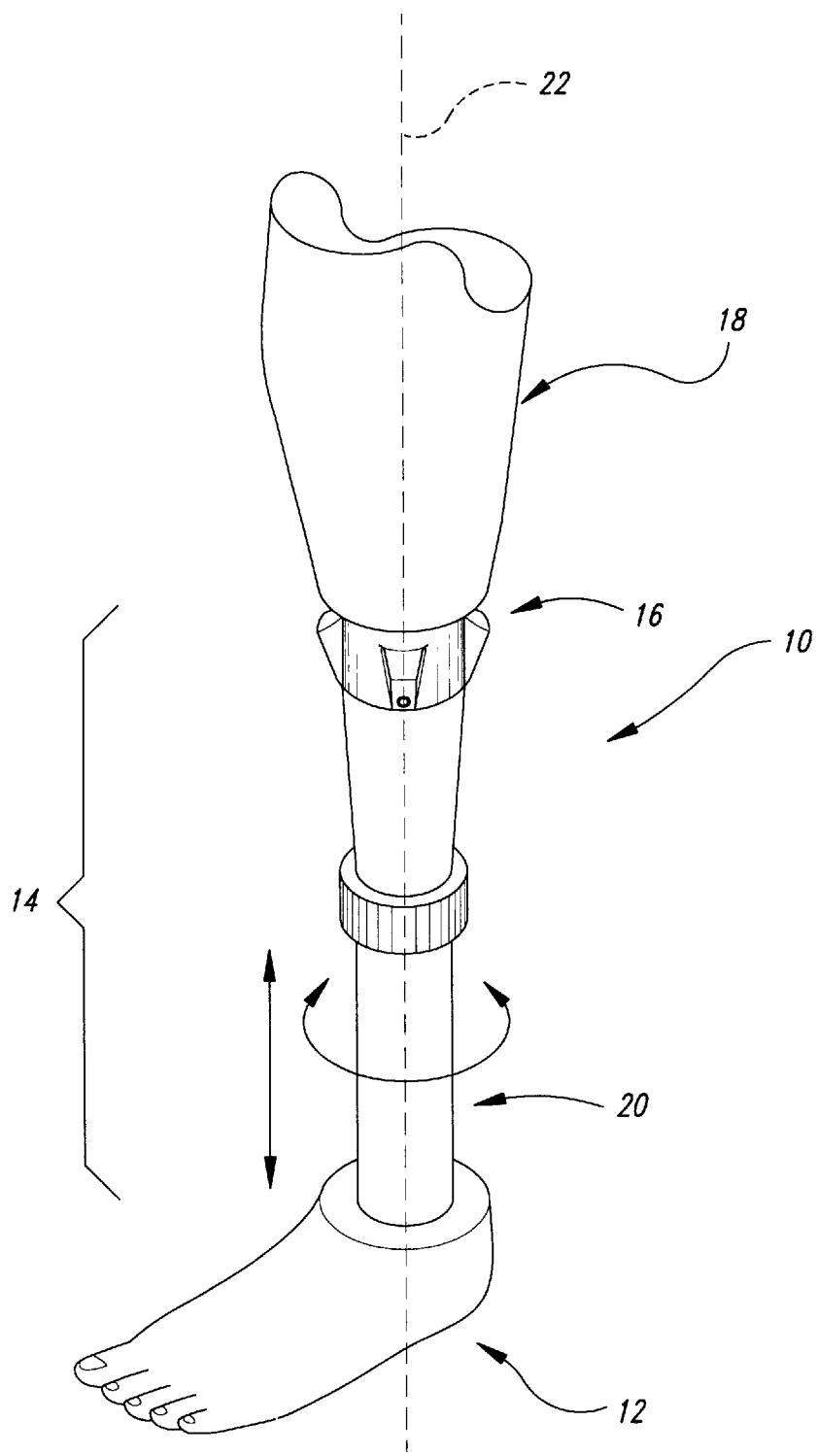
FIG. 1 is an isometric view of a prosthetic system using the inventive pylon.

With reference to FIG. 1, a preferred embodiment of the present invention provides a prosthetic system 10 comprising a prosthetic foot 12 and a pylon 14. The pylon 14 has a first end portion 16 releasably connected to a conventional socket 18 into which a patient's leg stump fits, and a second end portion 20 releasably connected to the prosthetic foot 12. The second end portion 20 is rotatable relative to the first end portion 16 about a longitudinal axis 22 of the pylon 14, and is also axially movable relative to the first end portion 16.

Figure 2:
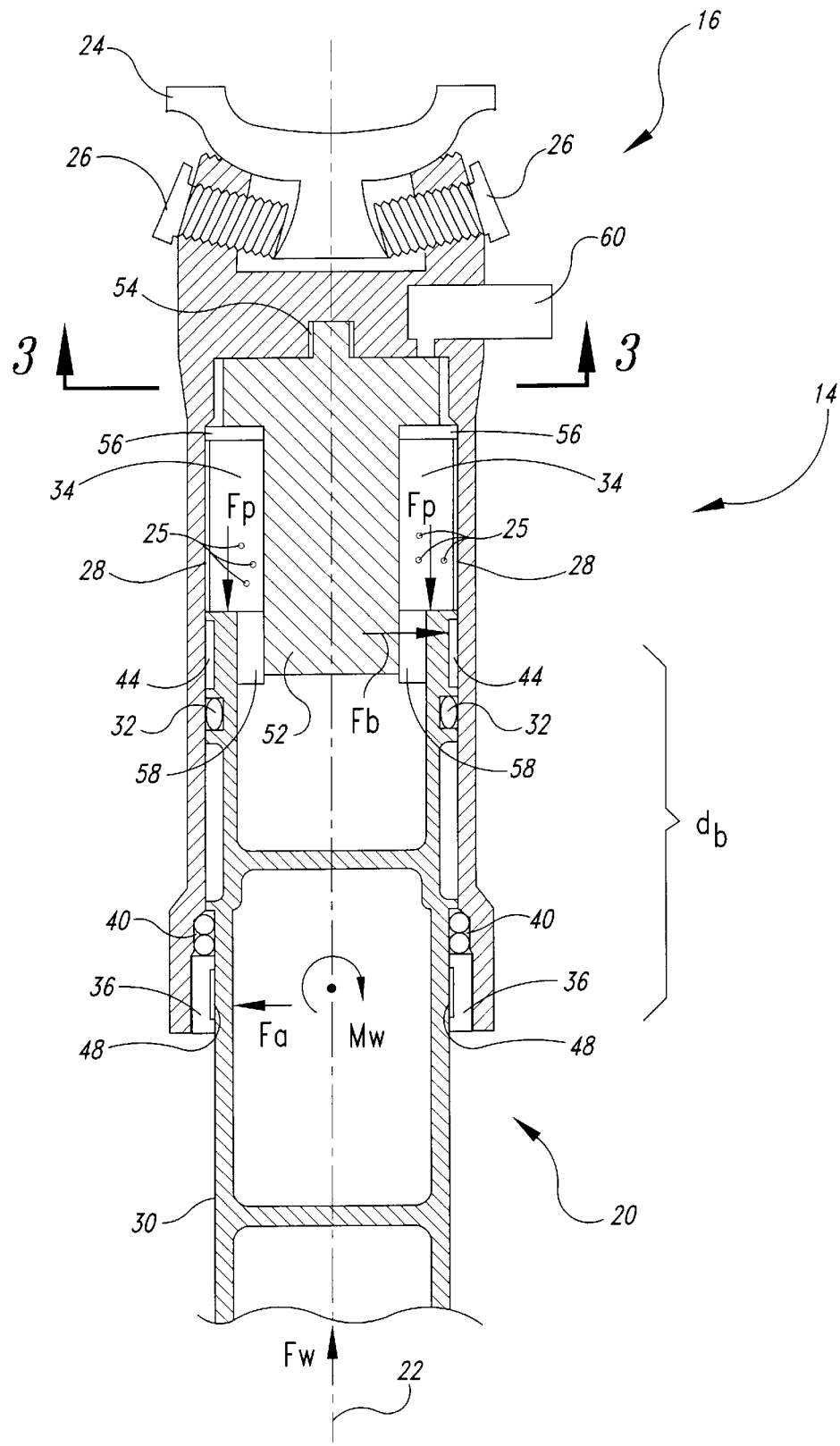
FIG. 2 is a side cross-sectional view of the inventive pylon of FIG. 1.

The pylon 14 of FIG. 1 is shown in more detail in FIG. 2. The first end portion 16 includes a conventional attachment plate 24 which attaches to the conventional socket (not shown in FIG. 2) in a well known manner. The angle of the attachment plate 24 may be adjusted with adjustment bolts 26.

The first end portion 16 also includes a piston chamber 28 receiving a piston 30. The piston chamber 28 is preferably made of aluminum or titanium, and the piston 30 is preferably made of titanium.

Figure 4:
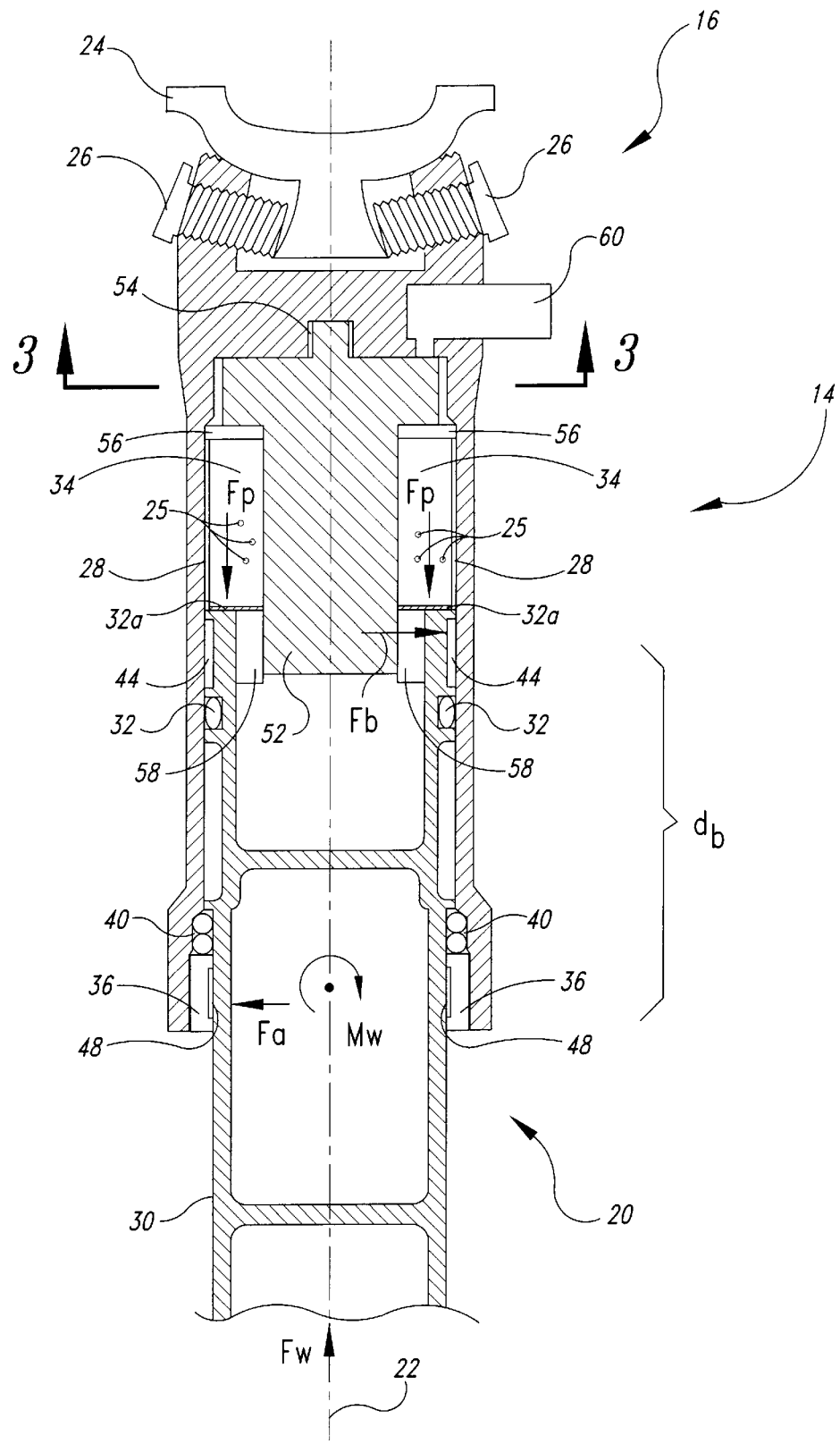
FIG. 4 is a side cross-sectional view of a pylon having a membrane in accordance with an embodiment of the invention.
Figure 5:
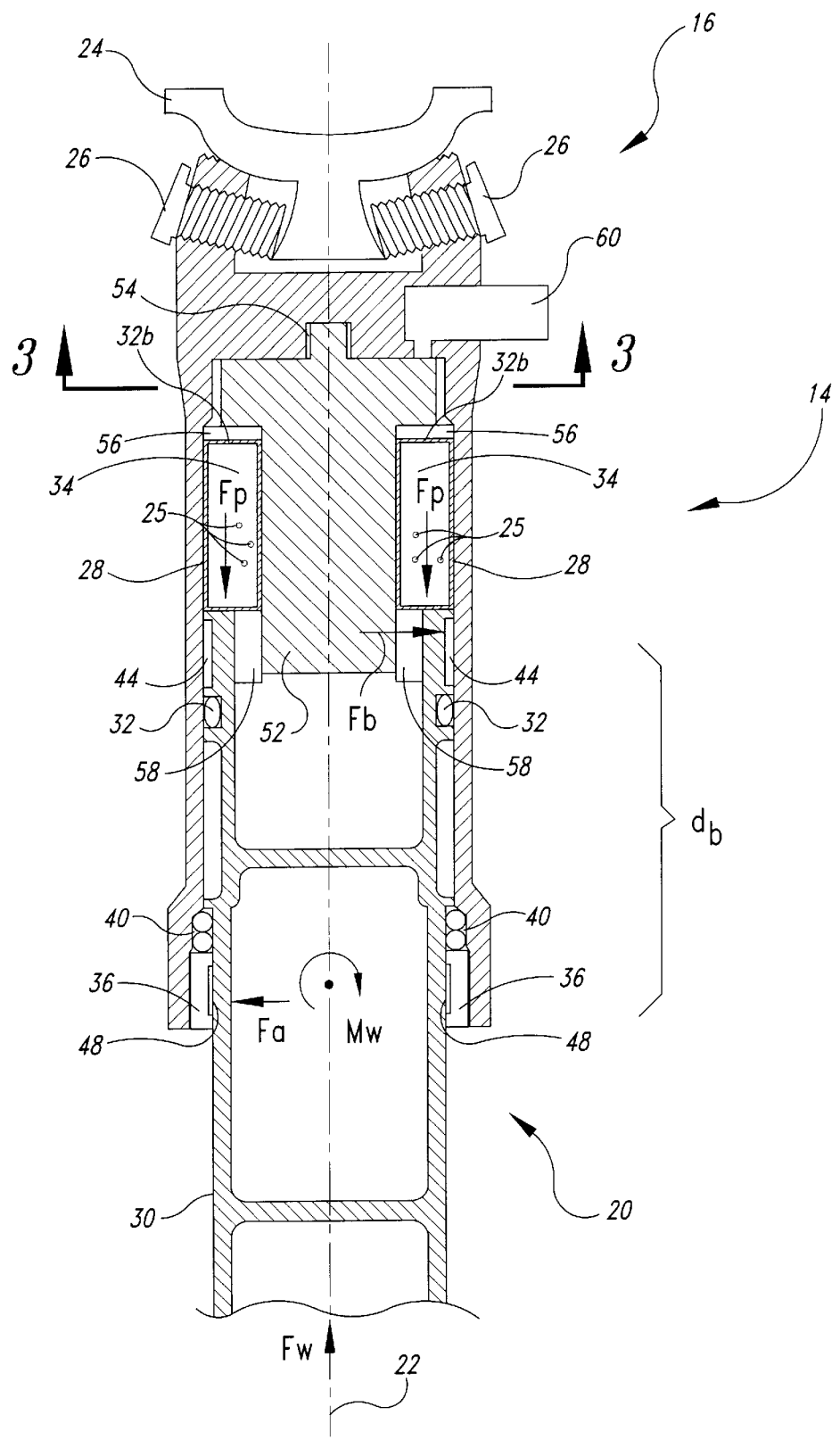
FIG. 5 is a side cross-sectional view of a pylon having a bladder in accordance with another embodiment of the invention.

The piston 30 has an O-ring seal 32 mounted in a groove about its circumference so that the piston chamber 28 contains an enclosed, sealed area 34. Alternatively, the piston chamber 28 can be enclosed and sealed by a membrane 32a (FIG. 4) attached to the inner walls of the piston chamber 28 and positioned orthogonally to the longitudinal axis 22. As another alternative, the piston chamber 28 can include a fluid bladder 32b (FIG. 5) which is enclosed and sealed.

A retainer block 36 retains the piston 30 in the piston chamber 28, and O-ring bumpers 40 cushion the impact of the piston 30 against the retainer block 36. A bearing, such as a wear ring 44, is mounted about the circumference of the piston 30 in contact with the inner walls of the piston chamber 28, and a bearing, such as a wear ring 48, is mounted in the retainer block 36 in contact with the piston 30. The wear rings 44 and 48 are preferably made of TURCITE-X®, and will be discussed in more detail below.

The pylon 14 also has a torsional spring including cushions (not shown in FIG. 2) and a torsion key 52 rotatably mounted at one end in a bearing 54 seated in an interior end of the piston chamber 28. The cushions and the torsion key 52 are retained by a stop plate 56. A slot in the head of the piston 30 receives the other end of the torsion key 52 in a torsion slide 58 preferably made of TURCITE-X®. As a result, the torsion key 52 slides into and out of the head of the piston 30 with little resistance, but it is forced to rotate in its bearing 54 against the cushions (not shown in FIG. 2) about the longitudinal axis 22 when the piston 30 rotates relative to the piston chamber 28. The torsion key 52 and cushions will be described in more detail below.

In operation, the area 34 contains a compressible volume of fluid, preferably air. However, the fluid can also be, for example, another compressible gas or an incompressible liquid containing compressible objects 25. Those having skill in the field of this invention will understand that a wide variety of compressible volumes of fluid fall within the scope of this invention. Also, it is preferable that the pylon 14 include a fitting 60 so that the compressible volume of fluid can be pressurized. This allows a patient to customize the response of the pylon 14.

As the patient moves forward, the heel of the prosthetic foot (not shown in FIG. 2) strikes the ground. This begins dorsi-flexal movement which, of course, is the period in the patient's gait in which the angle between the pylon 14 and the toes of the prosthetic foot decreases. During this period, a force $F_W$ due to the patient's weight is impressed on the piston 30, and the piston 30 slides into the piston chamber 28 resisted by a pressure force $F_P$ as the compressible volume of fluid compresses. As a result, substantially all of the patient's weight applied to the piston 30 is resiliently cushioned by the compressible volume of fluid.

At the same time, the torsion key 52 slides into the slot in the head of the piston 30. Also, the patient's movement impresses a moment on the piston 30 relative to the piston chamber 28 which may, for example, be resolved into a couple including a moment $M_W$ centered on the wear ring 48 and a force $F_a$ imposed on the wear ring 48. This moment $M_W$ impresses a force $F_b$ on the wear ring 44, for example, as follows:

$$F_b = (M_W/d_b) \quad (1)$$

where $d_b$ is the length of the moment arm at the wear ring 44. Because of the coefficients of friction $\mu_a, \mu_b$ between the wear rings 48 and 44 and the piston 30 and the inner wall of the piston chamber 28, respectively, the forces $F_a$ and $Fb$ cause the wear rings 44 and 48 to resist motion by the piston 30 with a friction force $F_F$ equal to:

$$F_F = (\mu_a * F_a + \mu_b F_b) \quad (2)$$

At a point during the patient's movement forward when the toes of the prosthetic foot (not shown in FIG. 2) are on the ground and the heel is beginning to rise, the force $F_W$ due to the patient's weight begins to lessen as the patient's weight shifts to the other leg. At the same time, the moment $M_W$ and the force $F_a$ reach their maximum.

At this point in the patient's gait, the patient begins to transition to plantar-flexal movement which, of course, is the period in the patient's gait when the angle between the pylon 14 and the toes of the prosthetic foot (not shown in FIG. 2) increases. The pressure force $F_P$ tries to urge the piston 30 out of the piston chamber 28, but the friction force $F_F$ (which is at its maximum because of the maximized moment $M_W$ and force $F_a$) advantageously restricts motion by the piston 30 for a moment despite the lessening in the force $F_W$.

When the moment $M_W$ and the force $F_a$ decrease from their maximum values as the patient continues forward, the friction force $F_F$ decreases sufficiently to allow the pressure force $F_P$ to rapidly urge the piston 30 out of the piston chamber 28. As a result, the patient receives an advantageous boost forward. The timing and amount of the boost can, of course, be controlled by varying the pressurization of the compressible volume of fluid through the fitting 60, by varying the length of the moment arm $d_b$, and by varying the coefficients of friction $\mu_a$ and $\mu_b$.

Figure 3:
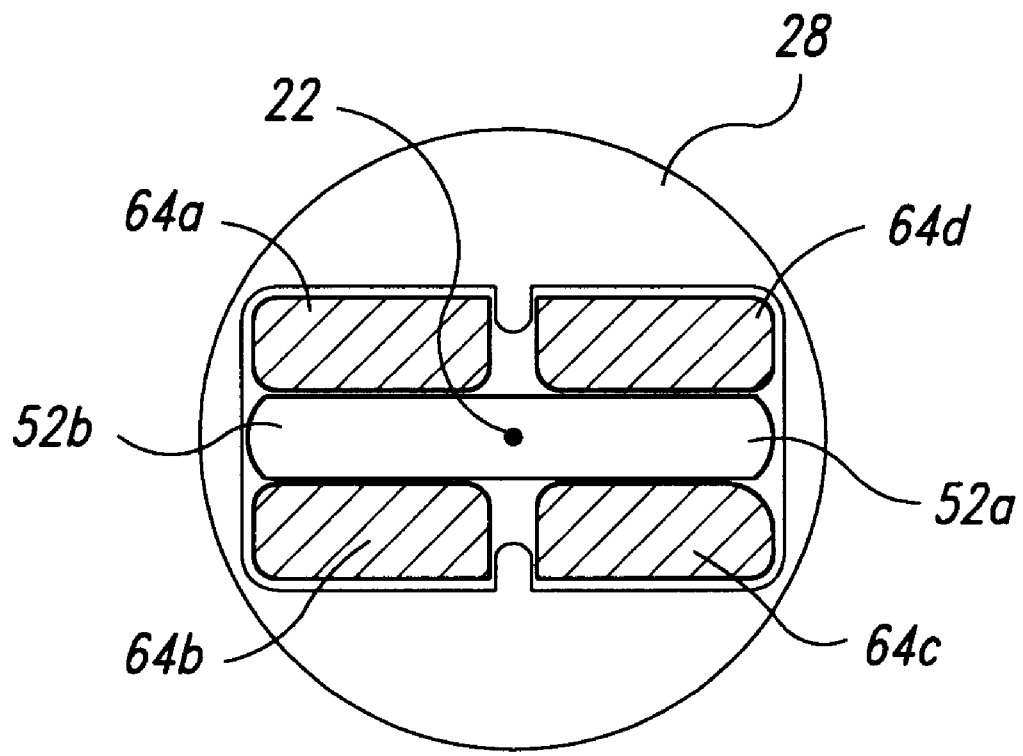
FIG. 3 is a plan cross-sectional view of a torsional spring of the inventive pylon of FIG. 1.

The torsion key 52 is shown in more detail in FIG. 3. It includes projections 52a and 52b which compress cushions 64a, 64b, 64c, 64d when the torsion key 52 is rotated by the piston (not shown in FIG. 3) about the longitudinal axis 22 of the pylon (not shown in FIG. 3). In this manner, the torsion key 52 resists rotation by the piston, and hence by the patient's leg stump (not shown in FIG. 3), about the longitudinal axis 22. The cushions 64a, 64b, 64c, 64d are preferably made of polyurethane, and they allow a range of rotation by the torsion key 52 of approximately ±15°.

In an alternative embodiment, the shapes, positions and spring rates of the cushions 64a, 64b, 64c, 64d may be selected so that the cushions 64a, 64b resist clockwise rotation by the torsion key 52 with a different force than they resist counter-clockwise rotation. It may, for example, be advantageous to have a different resistance to clockwise and counter-clockwise rotation according to whether the pylon (not shown in FIG. 3) is attached to a right or a left leg stump. Also, it will be understood that a wide variety of alternative configurations for the cushions are possible—including more or less than two cushions—and that these alternative configurations fall within the scope of the present invention.

The present invention thus advantageously provides a pylon which is cushioned and resilient. It also provides a patient a boost forward at an advantageous moment in their stride.

Although the present invention has been described with reference to a preferred embodiment, the invention is not limited to this preferred embodiment. Rather, the invention is limited only by the appended claims, which include within their scope all equivalent devices or methods which operate according to the principles of the invention as described.

We claim:

1. A pylon for a lower limb prosthesis having a leg stump and a prosthetic foot for supporting the weight of a patient, comprising:

a first end portion connectable to the leg stump;

a second end portion opposing the first end portion and connectable to the prosthetic foot, the second end portion being rotatable and axially movable relative to the first end portion about and along a longitudinal axis of the pylon, respectively;

an enclosed compressible volume of fluid coupling the first and second end portions, the compressible volume of fluid supporting and cushioning axial loads along the longitudinal axis of the pylon; and a torsional spring coupled to the first and second end portions, the torsional spring directly resisting relative rotation between the first and second end portions to bias the first and second end portions to a centered position, and the torsional spring allowing unrestricted axial movement between the first and second end portions.

2. The pylon of claim 1 wherein one of the first and second end portions includes a piston having a head, wherein the other of the first and second end portions includes a piston chamber for receiving the piston along the longitudinal axis of the pylon, and wherein the compressible volume of fluid is enclosed by the piston head and piston chamber.

3. The pylon of claim 2 wherein the piston has a seal circumferentially mounted thereon so that the piston head and piston seal together seal the portion of the piston chamber containing the compressible volume of fluid.

4. The pylon of claim 2 wherein the piston chamber has a membrane sealing the portion of the piston chamber containing the compressible volume of fluid.

5. The pylon of claim 2 wherein the compressible volume of fluid is sealed in a bladder contained in the piston chamber.

6. The pylon of claim 2 wherein the piston head has a slot therein, wherein the piston chamber has an interior end facing the piston head and also has interior walls, wherein the torsional spring comprises:

a torsion key having a first end rotatably mounted to the interior end of the piston chamber so that the torsion key is rotatable about the longitudinal axis of the pylon, the first end of the torsion key having projections extending radially from the rotation axis of the torsion key toward the interior walls of the piston chamber, the torsion key having a second end slidably engaging the piston head's slot so that relative rotation between the piston and the piston chamber rotates the torsion key; and one or more cushions positioned at the interior end of the piston chamber in close proximity to the projections at the first end of the torsion key so that the projections compress at least some of the cushions when relative rotation between the piston and the piston chamber rotates the torsion key.

7. The pylon of claim 1 wherein the compressible volume of fluid is enclosed and sealed so that it can be pressurized.

8. The pylon of claim 1 wherein the compressible volume of fluid comprises a compressible fluid.

9. The pylon of claim 1 wherein the compressible volume of fluid comprises an incompressible fluid containing compressible objects.

10. The pylon of claim 1 wherein the torsional spring is contained within the enclosed compressible volume of fluid.

11. The pylon of claim 1 wherein the enclosed compressible volume of fluid is compressed during dorsi-flexal movement of the prosthetic foot and is decompressed during the transition from dorsi-flexal to plantar-flexal movement of the prosthetic foot, wherein the pylon further comprises a bearing interposed between the first and second end portions such that it restricts the decompression of the enclosed compressible volume of fluid until an appropriate moment in the transition from dorsi-flexal to plantar-flexal movement of the prosthetic foot when the decompression will assist the patient in accelerating forward.

12. The pylon of claim 11 wherein one of the first and second end portions includes a piston having a head, wherein the other of the first and second end portions includes a piston chamber for receiving the piston along the longitudinal axis of the pylon, wherein the compressible volume of fluid is enclosed by the piston head and piston chamber, wherein the bearing comprises a wear band interposed between sides of the piston and interior walls of the piston chamber such that it momentarily restricts relative motion between the piston and the piston chamber along the longitudinal axis of the pylon when a sufficient moment is imparted to the piston relative to the piston chamber about a lateral axis of the piston during the transition from dorsi-flexal to plantar-flexal movement of the prosthetic foot.

13. The pylon of claim 1 wherein the torsional spring resists clockwise rotation with a first spring rate and wherein the torsional spring resists counter-clockwise rotation with a second spring rate that is selected to be different than the first spring rate in accordance with the patient's leg stump being either a right or left leg stump.

14. A prosthetic system for supporting the weight of a patient having a leg stump, the prosthetic system comprising:

a prosthetic foot; and a pylon comprising:

a first end portion connectable to the leg stump;

a second end portion opposing the first end portion and connectable to the prosthetic foot, the second end portion being rotatable and axially movable relative to the first end portion about and along a longitudinal axis of the pylon;

an enclosed compressible volume of fluid coupling the first and second end portions, the compressible volume of fluid supporting and cushioning axial loads along the longitudinal axis of the pylon; and a torsional spring coupled to the first and second end portions, the torsional spring directly resisting relative rotation between the first and second end portions without inducing axial forces between the first and second end portions to freely bias the first and second end portions to a centered position.

15. The prosthetic system of claim 14 wherein one of the first and second end portions of the pylon includes a piston having a head with a slot therein, wherein the other of the first and second end portions of the pylon includes a piston chamber for receiving the piston along the longitudinal axis of the pylon, the piston chamber having an interior end facing the piston head and also having interior walls, wherein the compressible volume of fluid is enclosed by the piston head and piston chamber, wherein the torsional spring comprises:

a torsion key having a first end rotatably mounted to the interior end of the piston chamber so that the torsion key is rotatable about the longitudinal axis of the pylon, the first end of the torsion key having projections extending radially from the rotation axis of the torsion key toward the interior walls of the piston chamber, the torsion key having a second end slidably engaging the piston head's slot so that relative rotation between the piston and the piston chamber rotates the torsion key; and one or more cushions positioned at the interior end of the piston chamber in close proximity to the projections at the first end of the torsion key so that the projections compress at least some of the cushions when relative rotation between the piston and the piston chamber rotates the torsion key.

16. The prosthetic system of claim 14 wherein the torsional spring is contained within the enclosed compressible volume of fluid.

17. The prosthetic system of claim 14 wherein the enclosed compressible volume of fluid is compressed during dorsi-flexal movement of the prosthetic foot and is decompressed during the transition from dorsi-flexal to plantar-flexal movement of the prosthetic foot, wherein the pylon further comprises a bearing interposed between the first and second end portions such that it restricts the decompression of the enclosed compressible volume of fluid until an appropriate moment in the transition from dorsi-flexal to plantar-flexal movement of the prosthetic foot when the decompression will assist the patient in accelerating forward.

18. A pylon for a lower limb prosthesis assembly, comprising:

a first member adapted to be connected to one of a leg socket or a prosthetic foot;

a second member adapted to be connected to the other of the leg socket or the prosthetic foot and coupled to the first member, the first and second members being rotatable with respect to one another about a longitudinal axis of the pylon, and the first and second members being axially moveable with respect to each other along the longitudinal axis of the pylon;

a compressible medium enclosed between the first and second members, the compressible medium supporting axial loads along the longitudinal axis of the pylon applied by a patient; and a rotational stabilizer having a first element and a second element, the first element being coupled to the first member in a manner in which the first element is axially fixed and rotatably moveable with respect to the first member, and the first element being coupled to the second member in a manner in which the first element is freely axially moveable and rotatably fixed with respect to second member, and wherein the second element is a biasing component positioned to restrict rotation of the first element with respect to the first member and bias the first element toward a centered position when rotation occurs between the first and second members.

19. The pylon of claim 18 wherein:

the first member has an interior end defining a chamber and the first element is rotatably attached to the first member within the chamber; and the second member has an end defining a piston head received within the chamber, the piston head having a slot axially receiving the first element to allow axial movement and prevent rotational movement between the second member and the first element.

20. The pylon of claim 19 wherein the compressible medium comprises a volume of compressible fluid enclosed between the first and second members, and the pylon further comprises a seal between the chamber of the first member and the piston head of the second member to seal the volume of fluid between the first and second members.

21. The pylon of claim 18 wherein:

the first member has a interior end defining a chamber and the first element is rotatably attached to the first member within the chamber;

the second member has an end defining a piston head received within the chamber, the piston head having a slot axially receiving the first element to allow axial movement and prevent rotational movement between the second member and the first element;

the first element is a rigid component; and the second element is positioned between the first member and the first element to engage the first element when the first and second members rotate with respect to one another and urge the first element into a centered position.

22. The pylon of claim 21 wherein:

the first element comprises a key rotatably mounted within the piston chamber so that the key is rotatable about the longitudinal axis of the pylon, the key having a first end with a plurality of projections extending radially outwardly toward an interior wall of the piston chamber and a second end slidably received in the slot of the piston head; and the second element comprises a compressible resilient member positioned in the piston chamber proximate to the projections of the first element, the compressible member being engageable with the projections at a first end of the first element when the first and second members rotate with respect to each other to allow limited rotation between the first and second members and urge the first and second members to a centered position.

23. The pylon of claim 22 wherein the compressible resilient member comprises a plurality of cushions.

24. A pylon for a lower limb prosthesis assembly, comprising:

a first member adapted to be connected to one of a leg socket or a prosthetic foot;

a second member adapted to be connected to the other of the leg socket or the prosthetic foot and coupled to the first member, the first and second members being rotatable with respect to one another about a longitudinal axis of the pylon, and the first and second members being axially moveable with respect to each other along the longitudinal axis of the pylon;

a compressible medium between the first and second members, the compressible medium supporting all axially compressive loads along the longitudinal axis of the pylon applied by a patient; and a rotational stabilizer coupled to the first and second members, the stabilizer having a first element coupled to the first and second members to allow unrestricted axial movement therebetween, and the stabilizer having a second element coupled to one of the first and second members to engage the first element in a manner that opposes rotation between the first and second members and biases the first and second members toward a centered position.

25. The pylon of claim 24 wherein:

the first member has an interior end defining a chamber and the first element is rotatably attached to the first member within the chamber; and the second member has an end defining a piston head received in the chamber of the first member, the piston head having a slot to axially receive the first element in a manner that allows axial movement and prevents rotational movement between the second member and the first element.

26. The pylon of claim 25 wherein the compressible medium comprises a volume of compressible fluid enclosed between the first and second members, and the pylon further comprises a seal between the chamber of the first member and the piston head of the second member to enclose the volume of fluid between the first and second members.

27. The pylon of claim 24 wherein:

the first member has an interior end defining a chamber and the first element is rotatably attached to the first member within the chamber;

the second member has an end defining a piston head received in the chamber of the first member, the piston head having a slot to axially receive the first element in a manner that allows axial movement and prevents rotational movement between the second member and the first element;

the first element is a rigid component; and the second element is a resilient member between the first member and the first element engage the first element when the first and second members rotate with respect to one another and urge the first element into a centered position.

28. The pylon of claim 27 wherein:

the first element comprises a key rotatably mounted to the interior end of the piston chamber so that the key is rotatable about the longitudinal axis of the pylon, the key having a first end with a plurality of projections extending radially outwardly toward an interior wall of the piston chamber and a second end slidably received in the slot of the piston head; and the compressible resilient member of the second element is positioned in the piston chamber proximate to the projections of the first element, the second element being engageable with the first end of the first element when the first and second members rotate with respect to each other to restrict rotation between the first and second members and urge the first and second members to a centered position.

29. The pylon of claim 28 wherein the compressible resilient member comprises a plurality of cushions positioned to engage the first end of the first element when the first and second members rotate with respect to one another.

* * * * *